(12) United States Patent
     Hananouchi

(10) Patent No.: US 11,147,504 B2
(45) Date of Patent: Oct. 19, 2021

(54) EXAMINATION DIAGNOSIS DEVICE

(71) Applicant: Osaka Sangyo University, Daito (JP)

(72) Inventor: Takehito Hananouchi, Daito (JP)

(73) Assignee: OSAKA SANGYO UNIVERSITY, Osaka (JP)

( * ) Notice: Subject to any disclaimer, the term of this patent is extended or adjusted under 35 U.S.C. 154(b) by 403 days.

(21) Appl. No.: 15/569,473

(22) PCT Filed: Mar. 29, 2016

(86) PCT No.: PCT/JP2016/001819
    § 371 (c)(1),
    (2) Date: Oct. 26, 2017

(87) PCT Pub. No.: WO2016/174819
    PCT Pub. Date: Nov. 3, 2016

(65) Prior Publication Data
     US 2018/0085049 A1    Mar. 29, 2018

(30) Foreign Application Priority Data
     Apr. 27, 2015  (JP) .............................. JP2015-090299

(51) Int. Cl.
     *A61B 5/00*      (2006.01)
     *A61B 1/317*     (2006.01)
     (Continued)

(52) U.S. Cl.
     CPC ............ *A61B 5/4528* (2013.01); *A61B 1/317* (2013.01); *A61B 5/1036* (2013.01);
     (Continued)

(58) Field of Classification Search
     CPC ... A61B 5/4528; A61B 5/6855; A61B 5/1036; A61B 1/317; A61B 2560/0443;
     (Continued)

(56) References Cited

U.S. PATENT DOCUMENTS 4,132,224 A * 1/1979 Randolph ............ A61B 5/0053
                                              600/587
4,503,865 A * 3/1985 Shishido .............. A61B 5/0057
                                              600/550
(Continued)

FOREIGN PATENT DOCUMENTS

JP     H09-510644 A     10/1997
JP     2000201906 A      7/2000
                (Continued)

OTHER PUBLICATIONS

Decision to Grant dated Nov. 7, 2017 in JP Application No. 2017-515371.

(Continued)

*Primary Examiner* — Jacqueline Cheng
*Assistant Examiner* — Tho Q Tran
(74) *Attorney, Agent, or Firm* — Panitch Schwarze Belisario & Nadel LLP

(57) ABSTRACT

An examination diagnosis device includes a probe, a stress detector and a grip. The probe has an elongated portion and a tip portion, and the tip portion is provided to be bent at one end of the elongated portion. The stress detector is configured to be able to detect a force in an X direction, a force in a Y direction and a force in a Z direction applied to the tip portion of the probe. The tip portion of the probe may be bent in a plane parallel to the X direction and the Z direction. A user allows the tip portion of the probe to come into contact with a joint portion that is a subject of examination and diagnosis while gripping the grip.

7 Claims, 11 Drawing Sheets

(51) Int. Cl.
*A61B 5/103* (2006.01)
*A61B 90/00* (2016.01)

(52) U.S. Cl.
CPC .......... *A61B 5/6855* (2013.01); *A61B 5/6885* (2013.01); *A61B 2090/064* (2016.02); *A61B 2505/05* (2013.01); *A61B 2560/0431* (2013.01); *A61B 2560/0443* (2013.01); *A61B 2562/0247* (2013.01); *A61B 2562/0252* (2013.01); *A61B 2562/0261* (2013.01)

(58) Field of Classification Search
CPC .......... A61B 2505/05; A61B 2090/064; A61B 5/6885; A61B 2562/0261; A61B 2562/0252; A61B 2562/0247; A61B 2560/0431; A61B 5/4514; A61B 5/4595; A61B 5/459; A61B 5/4576; A61B 5/458; A61B 5/45; A61B 5/4538; A61B 5/4533; A61B 5/4523
See application file for complete search history.

(56) References Cited

U.S. PATENT DOCUMENTS

| | | | | |
|---|---|---|---|---|
| 4,779,349 A * | 10/1988 | Odensten | ............... | A61B 1/317 33/512 |
| 5,433,215 A | 7/1995 | Athanasiou et al. | | |
| 5,482,055 A | 1/1996 | Smith | | |
| 5,503,162 A | 4/1996 | Athanasiou et al. | | |
| 5,673,708 A | 10/1997 | Athanasiou et al. | | |
| 5,904,658 A * | 5/1999 | Niederauer | .......... | A61B 5/0053 600/587 |
| 6,068,604 A * | 5/2000 | Krause | .................. | G01N 3/405 600/587 |
| 6,427,351 B1 * | 8/2002 | Matthews | ............ | A61B 5/1076 33/512 |
| 8,308,662 B2 * | 11/2012 | Lo | ........................ | A61B 5/1076 600/587 |
| 8,622,935 B1 * | 1/2014 | Leo | ....................... | A61B 5/6843 600/587 |
| 8,734,461 B2 * | 5/2014 | Ellis | ................... | A61B 17/1764 606/96 |
| 2006/0196280 A1 * | 9/2006 | Xi | ............................ | G01L 1/08 73/862.625 |
| 2007/0179381 A1 * | 8/2007 | Johansson | ............ | G01N 21/274 600/476 |
| 2013/0122466 A1 * | 5/2013 | Connor | ................ | A61B 5/4504 433/215 |

FOREIGN PATENT DOCUMENTS

| | | |
|---|---|---|
| JP | 2000517051 A | 12/2000 |
| JP | 2006110116 A | 4/2006 |

OTHER PUBLICATIONS

Int'l Search Report dated May 31, 2016 in Int'l Application No. PCT/JP2016/001819.
Iwamoto, "Treatment of Hip Joint Disease up-to-date", Seperate Volume of Ortho. Surgery, No. 57, pp. 105-108 (Apr. 10, 2010).
Byrd et al., "AANA Advanced Arthroscopy: The Hip", Elsevier, 4 pgs. (Jul. 6, 2010).
Biomomentum, Biomaterial and Cartilage Testing Solutions, ARTHRO-BST, Revolutionary Probe for Cartilage Evaluation, 3 pgs. (Mar. 25, 2015).

* cited by examiner

F I G. 4
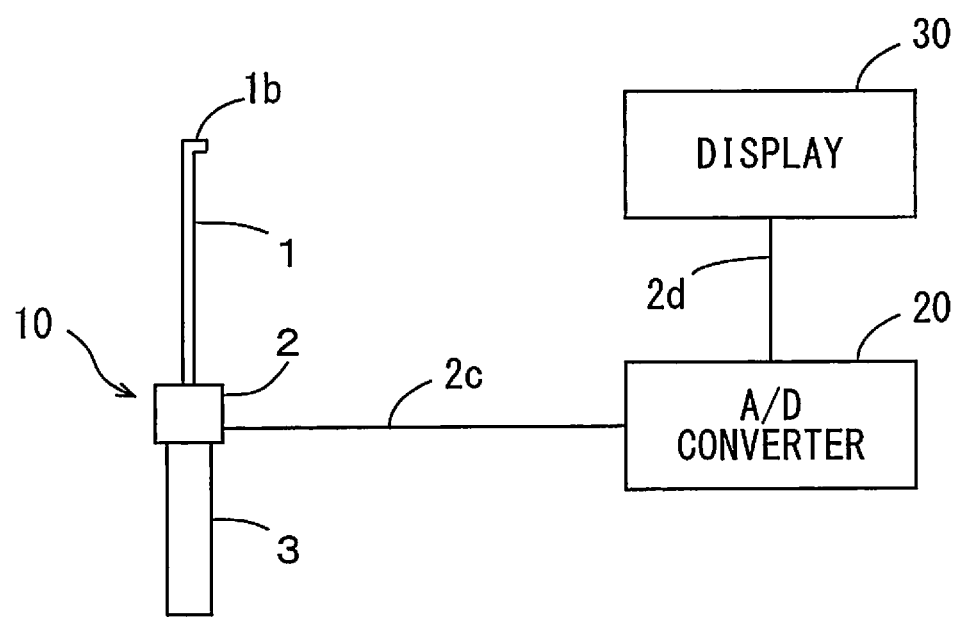

EXAMINATION DIAGNOSIS DEVICE

CROSS-REFERENCE TO RELATED APPLICATIONS

This application is a Section 371 of International Application No. PCT/JP2016/001819, filed Mar. 29, 2016, which was published in the Japanese language on Nov. 3, 2016, under International Publication No. WO 2016/174819 A1 and the disclosure of which is incorporated herein by reference.

TECHNICAL FIELD

The present invention relates to an examination diagnosis device for examining or diagnosing a condition of a joint portion.

BACKGROUND ART

As orthopedic surgery, there is arthroscopic surgery for treating tissue in a joint and its surrounding area. In the arthroscopic surgery, an arthroscope is inserted into the joint, and the surgery is performed while a clinical condition is checked.

In the arthroscopic surgery, tissue damage may be checked with use of a probe (see Non-Patent Documents 1, 2 and the like). For example, there is hip osteoarthritis as a representative example of hip joint disease that is to be treated in hip arthroscopic surgery. In recent years, it is being recognized that prodromal symptoms of the hip osteoarthritis appear in a labrum at a rim of a hip joint, and it has been found that the symptoms progress and disorder also occurs in a cartilage. Then, in identification of the clinical condition of the hip joint portion, the labrum is pulled, the cartilage is pushed, etc., by the probe, and presence and absence of damage and a degree of damage in the labrum and the cartilage are qualitatively evaluated.

PRIOR ART DOCUMENTS

Non Patent Literature

Non-Patent Document 1: Edited by Yukihide Iwamoto, "Treatment of Hip Joint Disease", Separate Volume of Orthopedics, Nankodo, year 2010, No. 57, p. 105-108

Non-Patent Document 2: J. W. Thomas Byrd and Carlos A. Guanche "AANA Advanced Arthroscopy: The Hip", (United States of America), Elsevier Inc., year 2010, p. 39, 41

SUMMARY OF INVENTION

Technical Problem

In the examination and diagnosis of the condition of the joint portion using the above-mentioned probe, a physician relies on his or her own sense based on the sensation applied to his or her hand from the probe. Thus, sufficient knowledge and experiences are required in order for the physician to carry out appropriate evaluation. Therefore, it is difficult for a physician with limited experience to appropriately make examination and diagnosis using the probe. Further, even an experienced physician cannot quantitatively evaluate a degree of improvement in a damaged site as a result of surgical procedure.

An object of the present invention is to provide an examination diagnosis device by which a user can efficiently and appropriately examine and diagnose a condition of a joint portion using a probe without depending on his or her skill.

Solution to Problem (1) An examination diagnosis device according to the present invention for examining or diagnosing a condition of a joint portion, includes a grip to be gripped by a user, a probe that is provided to extend in a first direction from the grip and has a bent tip portion, and a detector that detects a force applied to the tip portion of the probe in the first direction, and detects a force applied to the tip portion of the probe in a second direction intersecting with the first direction.

In this examination diagnosis device, the tip portion of the probe is allowed to come into contact with the joint portion while the grip is gripped by the user. The joint portion is pulled or pushed by the probe, so that a reaction force is applied to the tip portion of the probe from the joint portion. The force applied in the first direction and the force applied in the second direction to the tip portion of the probe from the joint portion are respectively detected by the detector.

Because the probe extends in the first direction, the reaction force of the joint portion against the pull or push corresponds to the force in the first direction. Therefore, the condition of the joint portion can be appropriately and quantitatively evaluated by the pull or push based on the detected force in the first direction. Further, the reaction force applied in a direction different from the first direction may be applied to the probe from the joint portion due to other factors. In the above-mentioned configuration, because the force applied in the second direction intersecting with the first direction is detected, the force applied to the tip portion of the probe due to other factors can be identified based on the detected force in the second direction. Therefore, the joint portion can be diversely evaluated. Thus, it is possible to efficiently and appropriately examine and diagnose the condition of the joint portion using the probe without depending on the skill of the user.

(2) The tip portion of the probe may be provided to be bent in a plane parallel to the first direction and the second direction. In this case, when the joint is pulled or pushed by the probe, the force applied to the tip portion of the probe in the second direction is relatively large. Thus, the force applied to the tip portion of the probe can be appropriately identified based on the detected force in the second direction.

(3) The detector may detect a force applied to the tip portion of the probe in a third direction intersecting with the first direction and the second direction. In this case, the joint portion can be more diversely evaluated based on the detected force in the third direction.

(4) The examination diagnosis device may further include a support member that supports the grip with the grip movable in the first direction and is to be gripped by the user together with the grip, and a movement amount measuring portion for measuring a movement amount of the support member with respect to the grip.

In this case, the user can identify the movement amount of the grip in the first direction, thereby being able to easily adjust a length of pulling the probe and a length of pushing the probe to certain lengths. Thus, it is possible to identify the force applied to the tip portion of the probe while ensuring reproducibility of the movement amount of the probe during the examination and diagnosis. As a result, the condition of the joint portion can be more accurately evaluated by pulling and pushing.

Advantageous Effects of Invention

The present invention enables efficient and appropriate evaluation of the joint portion with the use of the probe without dependence on the skill of the user.

BRIEF DESCRIPTION OF DRAWINGS

FIG. 4 is a diagram for explaining external devices connected to the examination diagnosis device.

DESCRIPTION OF EMBODIMENTS

An examination diagnosis device according to embodiments of the present invention will be described below with reference to drawings.

(1) Configuration of First Embodiment

Figure 1:
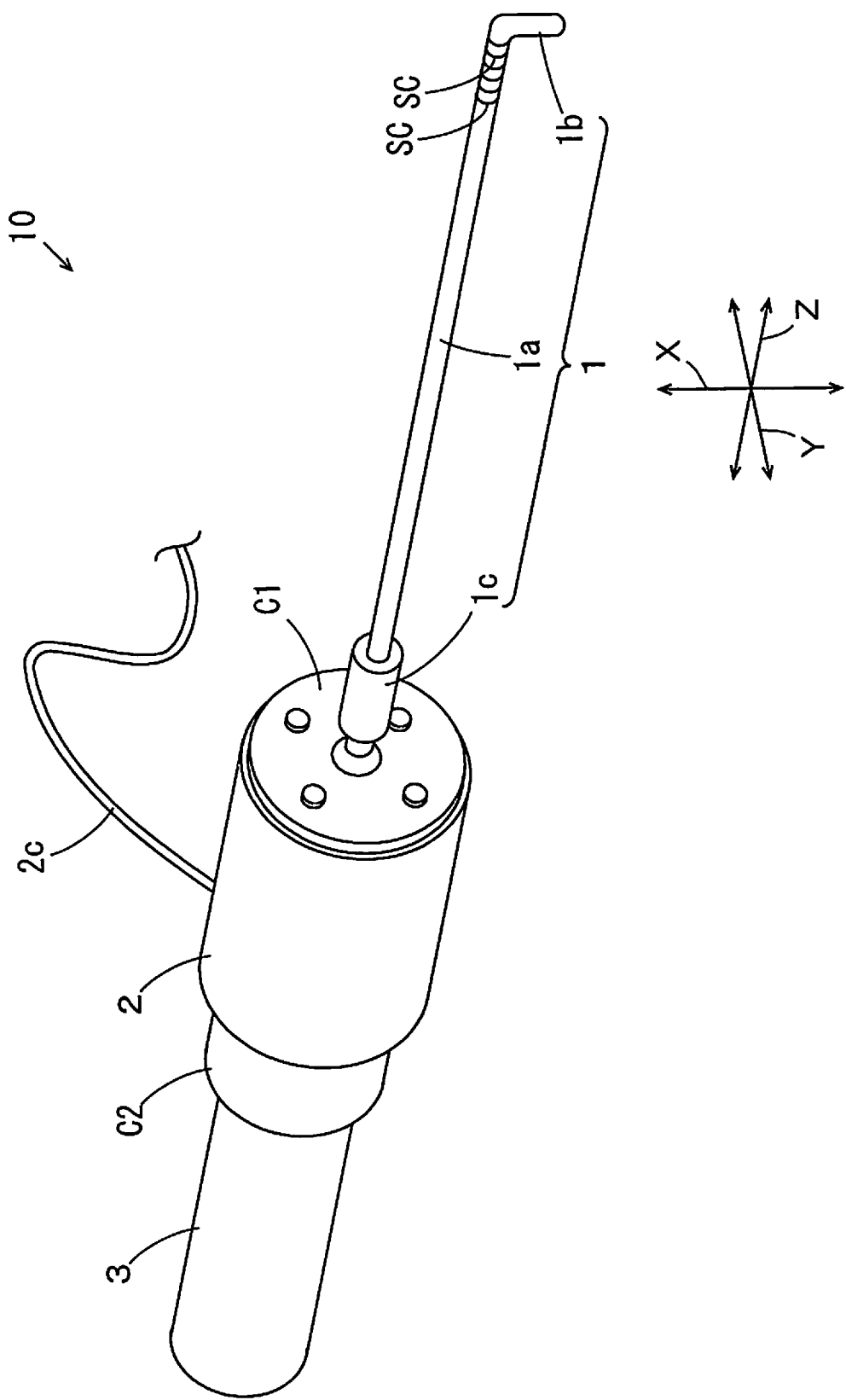
FIG. 1 is an external perspective view of an examination diagnosis device according to a first embodiment.
Figure 2:
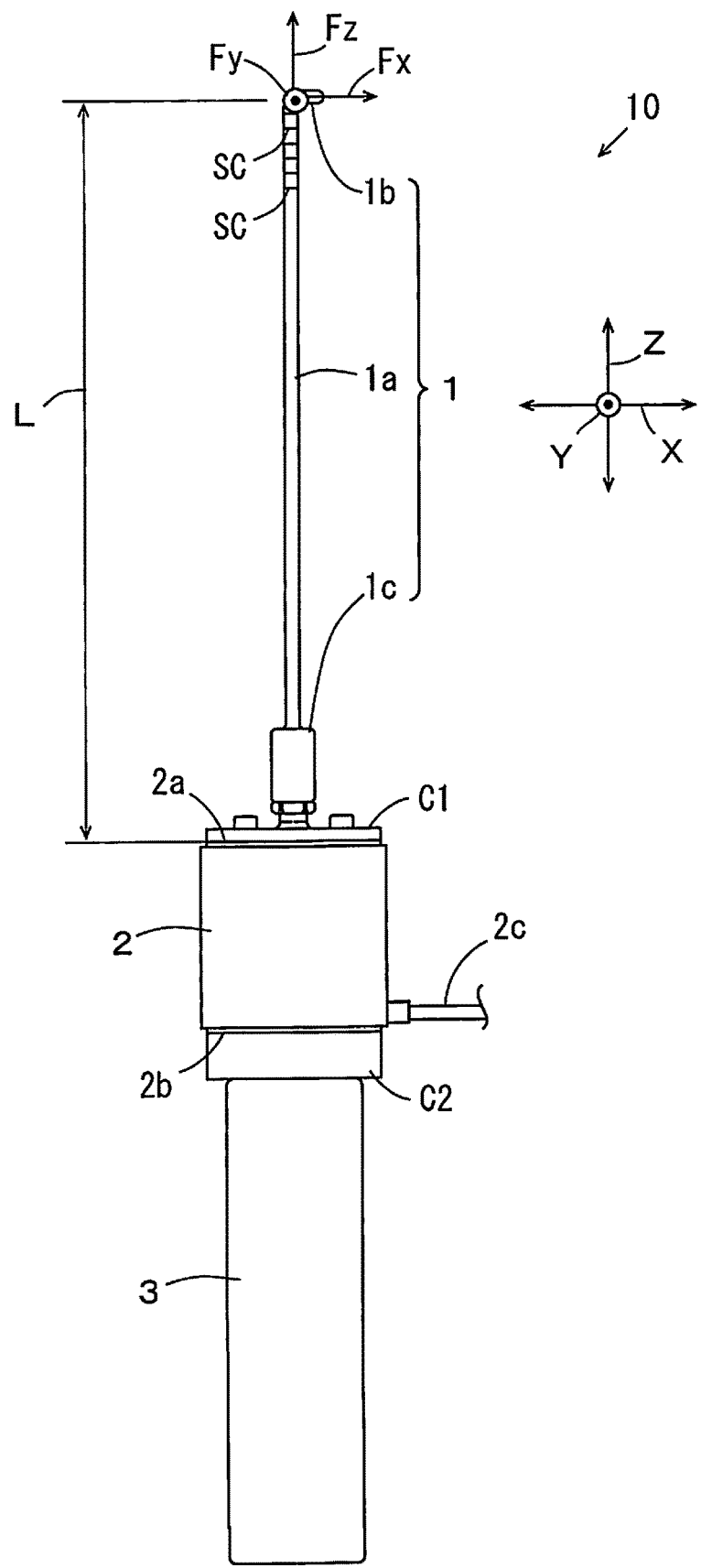
FIG. 2 is a side view of the examination diagnosis device of FIG. 1.

FIG. 1 is an external perspective view of the examination diagnosis device 10 according to the first embodiment, and FIG. 2 is a side view of the examination diagnosis device 10 of FIG. 1. As shown in FIGS. 1 and 2, the examination diagnosis device 10 includes a probe 1, a stress detector 2 and a grip 3.

The probe 1 has an elongated portion 1a, a tip portion 1b and an attachment portion 1c. The elongated portion 1a extends linearly. The tip portion 1b is provided to be bent at one end of the elongated portion 1a. The attachment portion 1c is provided at the other end of the elongated portion 1a. The probe 1 is preferably formed of a highly anti-corrosive material, and is formed of a stainless steel, for example. The probe 1 may be formed of another material such as another metal or resin.

In the present embodiment, a direction parallel to the elongated portion 1a is defined as a Z direction, and two directions perpendicular to the Z direction and orthogonal to each other are respectively defined as an X direction and a Y direction. In FIGS. 1 and 2, and below-mentioned FIGS. 3 and 6A and 6B, arrows respectively indicating the X direction, Y direction and the Z direction are provided. In the present example, the tip portion 1b is bent perpendicularly at the one end of the elongated portion 1a to extend in the X direction. In this case, the tip portion 1b is bent in a plane parallel to the X direction and the Z direction.

The tip portion 1b of the probe 1 comes into contact with a joint portion that is a subject of examination and diagnosis. The joint portion means tissue in a joint and around the joint. A specific example of the joint portion will be described below. In a portion of the elongated portion 1a in the vicinity of the tip portion 1b, a plurality of scale marks SC are inscribed at constant intervals. Each distance between the scale marks SC is 5 mm, for example. The user easily identifies an actual dimension in the joint portion by using the scale marks SC provided on the probe 1 as guides when making examination and diagnosis using the examination diagnosis device 10 while observing the joint portion using an arthroscope, for example.

As shown in FIG. 2, the stress detector 2 has a pressure-receiving surface 2a and a fixing surface 2b that are parallel to the X direction and the Y direction. The probe 1 is attached to a center portion of the pressure-receiving surface 2a of the stress detector 2 with a plate-shape connection member C1. A cable 2c is provided to extend from the stress detector 2.

The stress detector 2 is configured to be able to detect a force Fx in the X direction, a force Fy in the Y direction and a force Fz in the Z direction applied to the tip portion 1b of the probe 1. In the present embodiment, the stress detector 2 is a three-component force strain gauge type load cell, and includes a strain body (resilient element), and first, second and third strain gauges. The first strain gauge is bonded to the strain body to extend in the X direction, the second strain gauge is bonded to the strain body to extend in the Y direction, and the third strain gauge is bonded to the strain body to extend in the Z direction. When the force is applied to the probe 1, the force is applied to the pressure-receiving surface 2a via the connection member C1, so that strain is caused. The force in the X direction, the force in the Y direction and the force in the Z direction are detected by the first, second and third strain gauges based on the strain, and are output through the cable 2c in the form of analog electric signals. The analog electric signals output to the cable 2c are calibrated in advance to indicate the force Fx in the X direction, the force Fy in the Y direction and the force Fz in the Z direction applied to the tip portion 1b of the probe 1.

The grip 3 is provided to have a columnar shape and extend in the Z direction, and fixed to the fixing surface 2b of the stress detector 2 with the connection member C2. In the present example, an axial center of the grip 3 and an axial center of the elongated portion 1a of the probe 1 are positioned on a common straight line. The user allows the tip portion 1b of the probe 1 to come into contact with the joint portion while gripping the grip 3. The grip 3 is not limited to be a column and may be in another shape such as a flat shape or a curved shape. Further, irregularities or the like may be formed on a surface of the grip 3 to assist the user in easily gripping the grip 3.

Figure 3:
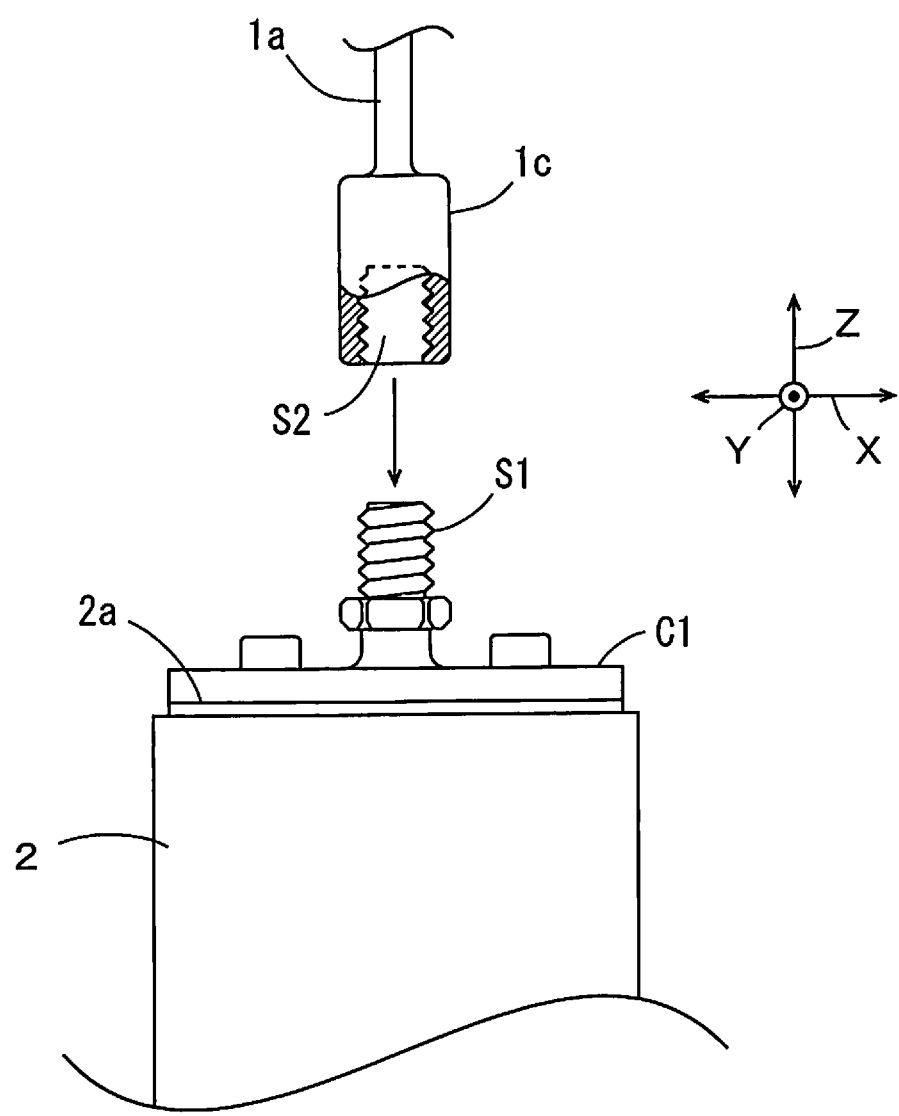
FIG. 3 is a diagram for explaining attachment of a probe.

FIG. 3 is a diagram for explaining the attachment of the probe 1. As shown in FIG. 3, the connection member C1 is fixed to the pressure-receiving surface 2a of the stress detector 2. An external thread S1 is formed at a center portion of the connection member C1 to project in the Z direction. An internal thread S2 corresponding to the external thread S1 is formed in the attachment portion 1c of the probe 1. The external thread S1 of the connection member C1 threadly engages with the internal thread S2 of the attachment portion 1c, so that the probe 1 is fixed to the connection member C1.

In this manner, the probe 1 is easily attachable to and detachable from the stress detector 2. Thus, the probe 1 can be easily cleaned, sterilized, disinfected, etc. Further, the used probe 1 can be easily replaced with a probe 1 that has been cleaned, sterilized, disinfected, etc. Further, a plurality of types of probes 1 can be selectively used as described below.

FIG. 4 is a diagram for explaining external devices connected to the examination diagnosis device 10. As shown in FIG. 4, the examination diagnosis device 10 is connected to an A/D (analog-digital) converter 20 through the cable 2c, and the A/D converter 20 is connected to a display 30 through a cable 2d.

The A/D converter 20 converts the analog electric signals output from the stress detector 2 into digital signals, and supplies the digital signals to the display 30. The display 30 includes a liquid crystal display, for example, and displays the forces Fx, Fy, Fz detected by the examination diagnosis device 10 based on the digital signals supplied from the A/D converter 20.

(2) Joint Portion

Figure 5A:
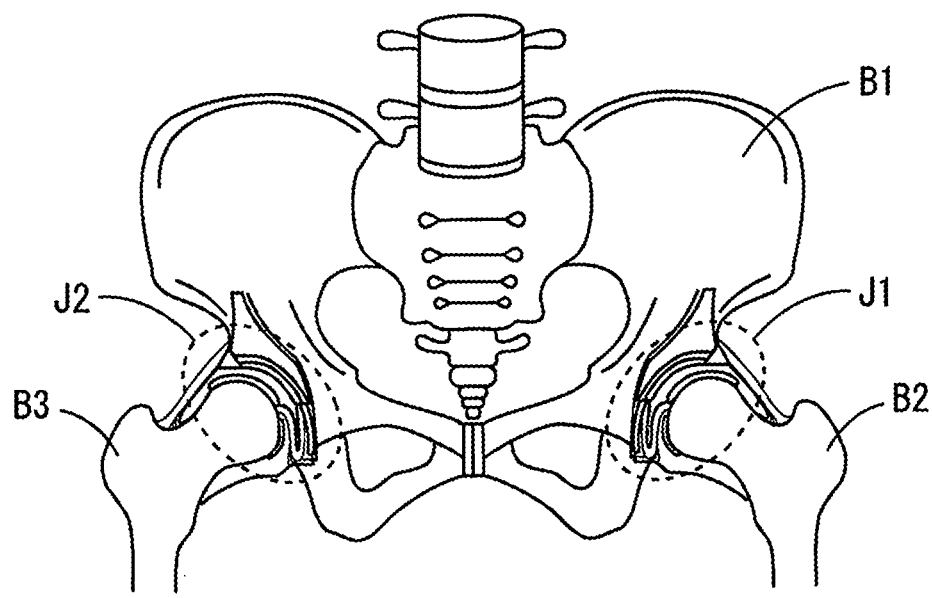
FIGS. 5A and 5B are diagrams for explaining a hip joint and its surrounding area.
Figure 5B:
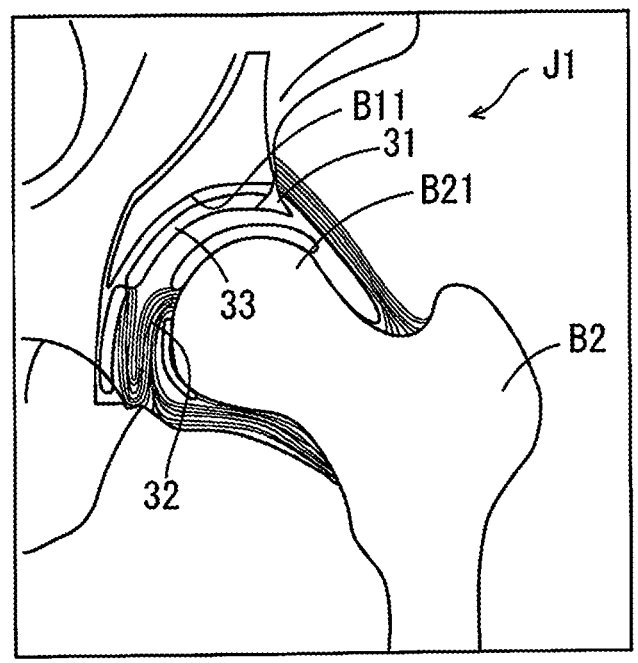

As a specific example of the joint portion, a hip joint and its surrounding area will be described below. FIGS. 5A and 5B are diagrams for explaining the hip joint and its surrounding area. FIG. 5A shows bone structure including left and right hip joints. FIG. 5B is an enlarged diagram of a left hip joint.

As shown in FIG. 5A, there is the left hip joint J1 between a pelvis B1 and a left femur B2, and there is the right hip joint J2 between the pelvis B1 and a right femur B3. The left hip joint J1 will be described below as one representative example. As shown in FIG. 5B, the left hip joint J1 is constituted by an acetabulum B11 of the pelvis B1 and a femoral head B21 of the left femur B2. There is a labrum 31 at a rim of the acetabulum B11. There are various types of tissue such as a femur ligament 32 and cartilage 33 in the left hip joint J1 and around the left hip joint J1.

The examination diagnosis device 10 is used for examination and diagnosis of the condition of the labrum 31, which is the tissue in each of the hip joints J1, J2, for example. A subject of the examination and diagnosis is not limited to the labrum 31, but may be various types of tissue such as a ligament and cartilage in the hip joints J1, J2 or around the hip joints J1, J2. Further, the joint portion, which is the subject of the examination and diagnosis, is not limited to the tissue in the hip joints J1, J2 and around the hip joints J1, J2, but may be tissue in another joint such as a knee joint or a shoulder joint or tissue around the other joint.

(3) Examination and Diagnosis

Figure 6A:
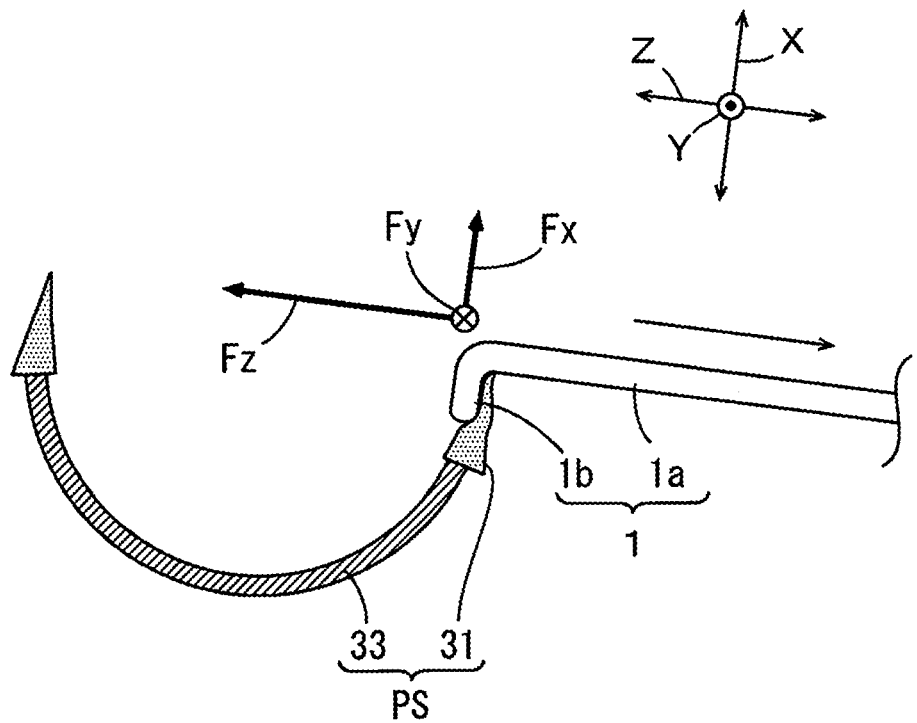
FIGS. 6A and 6B are schematic diagrams for explaining examples of examination and diagnosis of a condition of a joint portion by the examination diagnosis device.
Figure 6B:
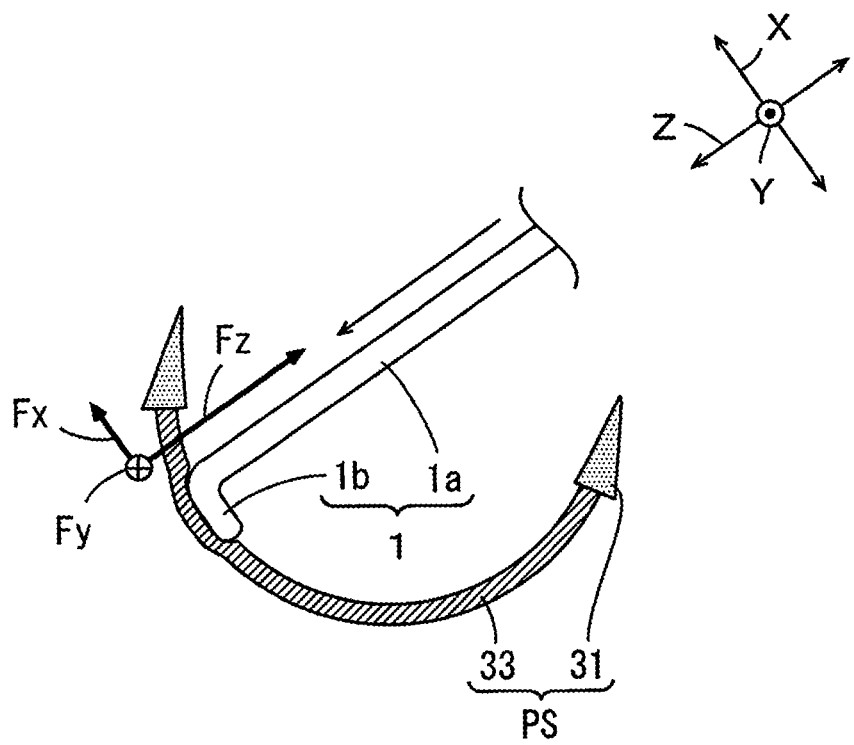

FIGS. 6A and 6B are schematic diagrams for explaining examples of the examination and diagnosis of the condition of the joint portion by the examination diagnosis device 10. In the example of FIGS. 6A and 6B, examination and diagnosis of the condition of a site PS that corresponds to the joint portion are made. The site PS includes the labrum 31 and the cartilage 33 of FIG. 5B, and is curved in a concave shape.

In the example of FIG. 6A, with the tip portion 1b of the probe 1 hooked to the labrum 31, the probe 1 is pulled towards the user. Thus, the labrum 31 is pulled. In the example of FIG. 6B, the tip portion 1b of the probe 1 is pressed against the cartilage 33. Thus, the cartilage 33 is pushed. Alternatively, the labrum 31 may be pushed by the probe 1. Normally, the tip portion 1b of the probe 1 is pressed against an outer surface of the labrum 31, so that the labrum 31 is pushed.

In this manner, the site PS is pulled or pushed by the probe 1, whereby a reaction force is applied to the tip portion 1b of the probe 1 from the site PS. The reaction force applied from the site PS is divided into the force Fx in the X direction, the force Fy in the Y direction and the force Fz in the Z direction.

In the example of FIG. 6A, the force Fz applied in a direction away from the pressure-receiving surface 2a (FIG. 2) of the stress detector 2 is exerted in the Z direction against the pull of the labrum 31. Further, the tip portion 1b is pressed against a rim of the labrum 31 to be hooked to the labrum 31. Therefore, the force Fx applied in a direction opposite to a bending direction of the tip portion 1b is exerted in the X direction. Further, the force Fy in the Y direction is exerted due to a shape of the labrum 31, a pulling direction of the probe 1 and the like. In the example of FIG. 6B, the force Fz applied in a direction towards the pressure-receiving surface 2a (FIG. 2) of the stress detector 2 is exerted in the Z direction against the push of the cartilage 33. Further, the force Fx in the X direction and the force Fy in the Y direction are exerted due to a shape of the cartilage 33, a pushing direction of the probe 1 and the like. The forces Fx, Fy, Fz applied to the tip portion 1b of the probe 1 from the joint portion in this manner are detected by the stress detector 2 of FIG. 2.

Figure 7:
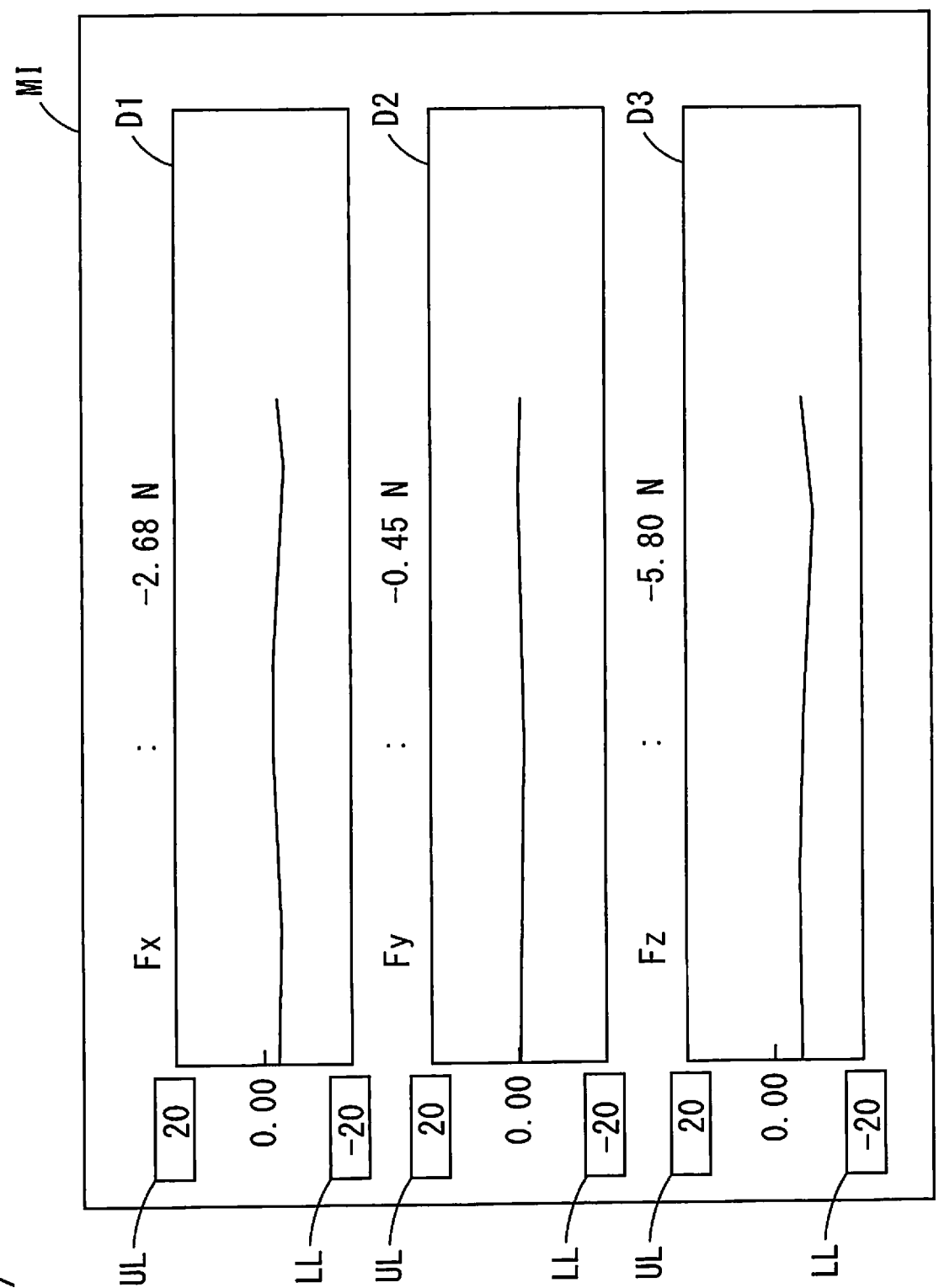
FIG. 7 is a diagram showing one example of a measurement screen.

The display 30 of FIG. 4 displays a measurement image indicating the detected forces Fx, Fy, Fz. FIG. 7 is a diagram showing one example of the measurement image. The measurement image M1 of FIG. 7 includes waveform display portions D1, D2, D3. In each of the waveform display portions D1 to D3, the abscissa indicates the time, and the ordinate indicates the magnitude of the force. A waveform indicating the change of the force Fx with time is displayed in the waveform display portion D1, a waveform indicating the change of the force Fy with time is displayed in the waveform display portion D2, and a waveform indicating the change of the force Fz with time is displayed in the waveform display portion D3.

A numerical value indicating the force Fx is displayed above the waveform display portion D1, a numerical value indicating the force Fy is displayed above the waveform display portion D2, and a numerical value indicating the force Fz is displayed above the waveform display portion D3. These numerical values may be numerical values measured at the latest detection time point, or may be numerical values measured at any time point designated by the user.

For example, the force Fz (the force Fz in FIG. 6B applied in a direction towards the pressure-receiving surface 2a is indicated by a positive value, and the force Fz (the force Fz of FIG. 6A applied in the opposite direction is indicated by a negative value. Further, the force Fx applied in the bending direction of the tip portion 1b is indicated by a positive value, and the force Fx (the force Fx of FIG. 6A applied in the opposite direction is indicated by a negative value. Further, the force Fy applied in one direction in the Y direction is indicated by a positive value, and the force Fy applied in the other direction in the Y direction is indicated by a negative value.

In the example of FIG. 7, the forces Fx, Fy, Fz applied in the case where the joint portion is pulled by the probe 1 are shown. In this case, as described above, the force Fz applied in the direction away from the pressure-receiving surface 2a, and the force Fx applied in the direction opposite to the bending direction of the tip portion 1b are exerted, so that the forces Fz, Fx are respectively indicated by negative values.

In the case where the joint portion is pulled or pushed, there is a certain correlation between the force Fz in the Z direction and the condition of the joint portion. For example, in the case where a degree of damage of the joint portion is large, the reaction force of the joint portion against the pull or push is likely to be small, so that the force Fz is likely to be small. Therefore, presence and absence of damage of the joint portion or the degree of damage can be evaluated based on the force Fz. Further, the force applied to the tip portion 1b of the probe 1 from the joint portion due to other factors can be identified based on the displayed forces Fx, Fy.

An upper limit value setting portion UL and a lower limit value setting portion LL are displayed at the left of each of the waveform display portions D1 to D3. Upper limit values of the forces Fx, Fy, Fz displayed in the waveform display portions D1 to D3 are set in the upper limit setting portion UL, and lower limit values of the forces Fx, Fy, Fz displayed in the waveform display portions D1 to D3 are set in the lower limit value setting portion LL. It is possible to change dynamic ranges of the waveforms displayed in the waveform display portions D1 to D3 by changing these upper limit values and lower limit values.

(4) Effects

In the examination and diagnosis by which a conventional probe is used, the force perceived by the user with his or her hand is a total force of the forces applied in various directions, and does not quantitatively indicate a reaction force applied from the joint portion to the probe in each direction. In contrast, in the examination diagnosis device 10 according to the present embodiment, the force Fx in the X direction, the force Fy in the Y direction and the force Fz in the Z direction applied to the tip portion 1b of the probe 1 are respectively detected. In this case, presence and absence of damage of the joint portion and a degree of damage can be appropriately and quantitatively evaluated based on the detected force Fz in the Z direction. Further, the force exerted on the tip portion 1b of the probe 1 from the joint portion due to a factor other than the pull and push can be identified based on the detected force Fx in the X direction and the detected force Fy in the Y direction. Therefore, the joint portion can be diversely evaluated. Thus, it is possible to efficiently and appropriately examine and diagnose the condition of the joint portion using the probe 1 without depending on the skill of the user.

(5) Other Shapes of Tip Portion

Figure 8A:
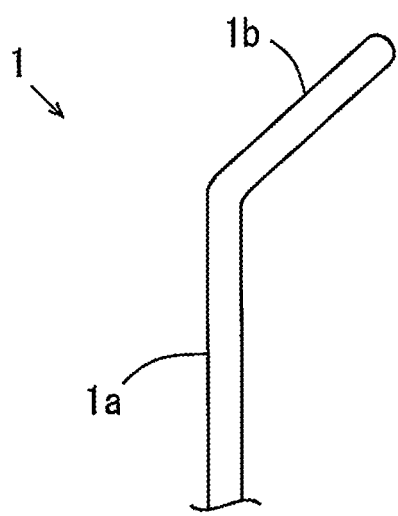
FIGS. 8A and 8B are diagrams showing examples of other shapes of a tip portion of a probe.
Figure 8B:
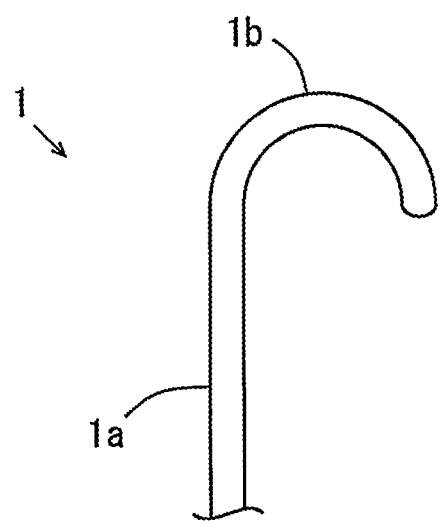

The shape of the tip portion 1b of the probe 1 is not limited to the above-mentioned example. FIGS. 8A and 8B are diagrams showing examples of other shapes of the tip portion 1b of the probe 1. In the example of FIG. 8A, the tip portion 1b is provided to form an obtuse angle with the elongated portion 1a. Further, in the example of FIG. 8B, the tip portion 1b is provided to be curved in a U-shape. It is possible to appropriately examine and diagnose the condition of joint portions having various shapes by selectively using the probes 1 having such various shapes.

(6) Second Embodiment

Figure 9:
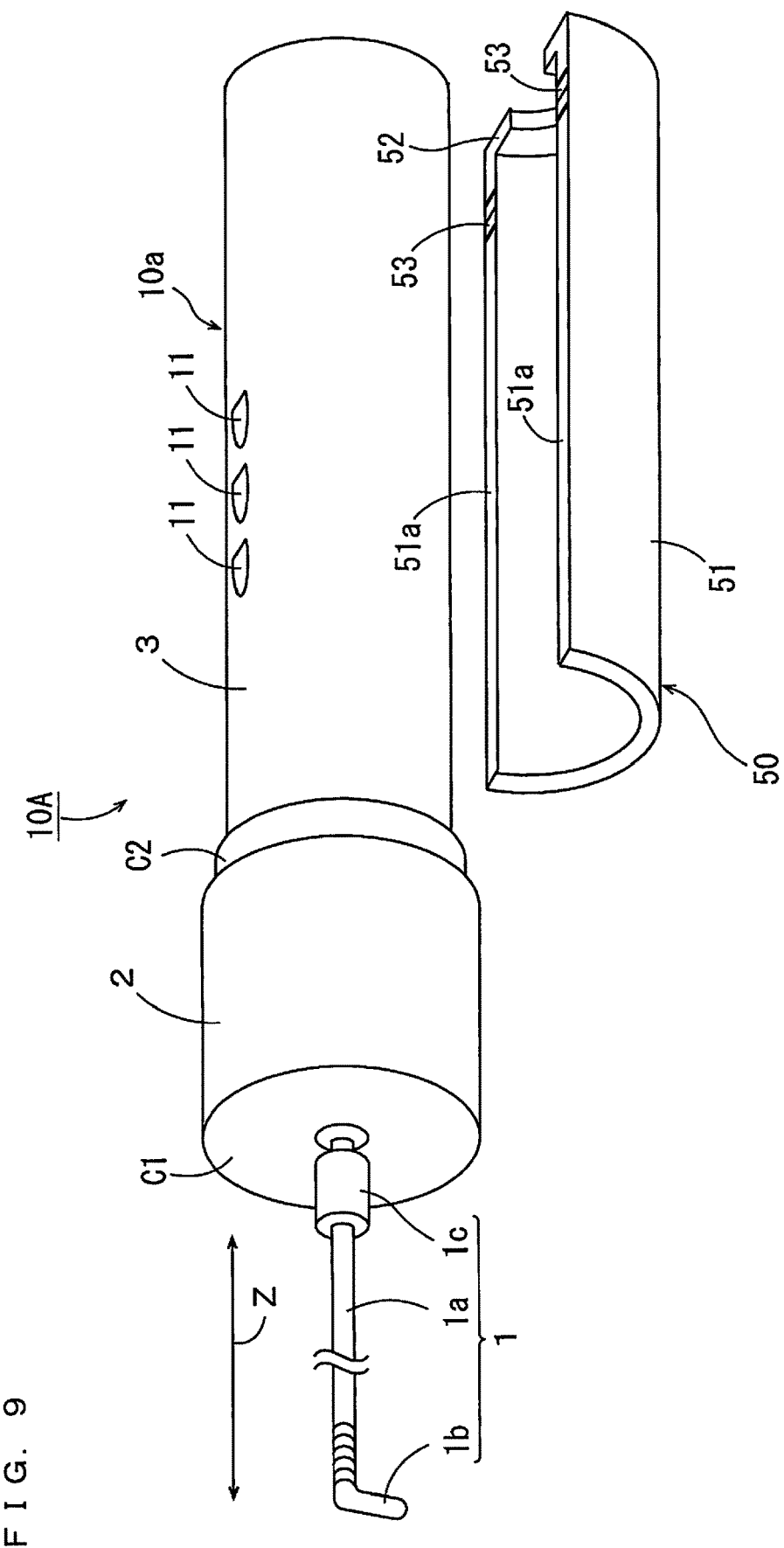
FIG. 9 is an external perspective view of an examination diagnosis device according to a second embodiment.

FIG. 9 is an external perspective view of an examination diagnosis device 10A according to the second embodiment. The examination diagnosis device 10A of FIG. 9 is constituted by a device main body 10a and a support member 50. The device main body 10a includes a probe 1, a stress detector 2 and a grip 3. One or a plurality of recesses 11 are formed at an outer peripheral surface of the grip 3 of the device main body 10a. The configuration of other parts of the device main body 10a is similar to the configuration of the examination diagnosis device 10 according to the first embodiment. The device main body 10a is connected to the A/D converter 20 and the display 30 shown in FIG. 4. Hereinafter, a direction towards the probe 1 of the device main body 10a is referred to as forward, and a direction away from the probe 1 is defined as rearward.

The support member 50 is formed of a light material such as a synthetic resin or aluminum. This support member 50 has a semi-cylindrical slider 51 and a substantially semicircular stopper 52. The slider 51 has a semi-cylindrical inner peripheral surface corresponding to an outer peripheral surface of the grip 3 of the device main body 10a. One end of the slider 51 is open, and the other end of the slider 51 is provided with the stopper 52. The slider 51 of the support member 50 supports the grip 3 of the device main body 10a movably in the Z direction. A shape of the slider 51 is not limited to a semi-cylindrical shape, and may be another shape as long as the slider 51 can support the grip 3 of the device main body 10a movably in the Z direction.

The support member 50 is used with the inner peripheral surface of the slider 51 directed upward. In the vicinity of the stopper 52 on upper end surfaces 51a of the slider 51, a pair of movement amount measuring portions 53 is provided. In the present embodiment, each movement amount measuring portion 53 includes a plurality of scale marks. One movement amount measuring portion 53 may be provided at the support member 50.

Figure 10:
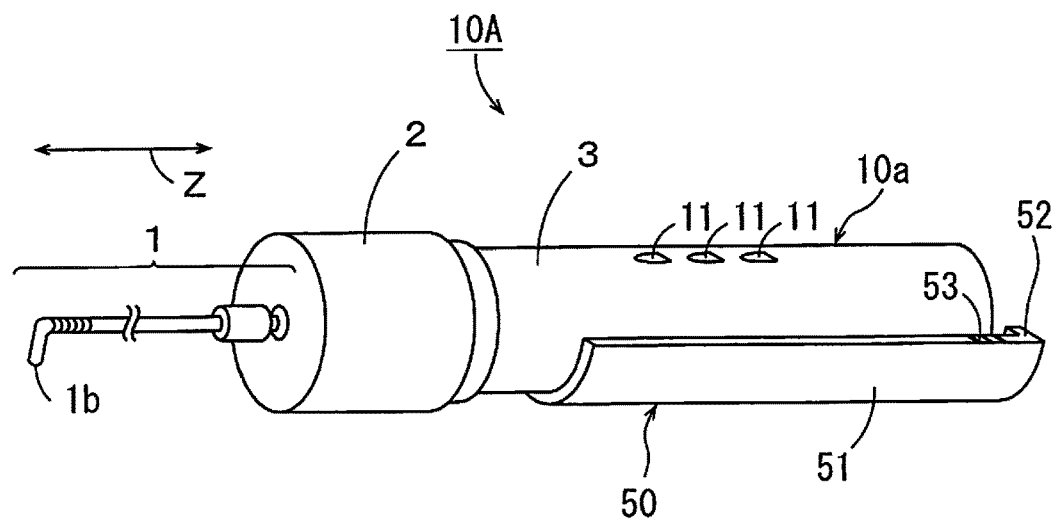
FIG. 10 is an external perspective view showing a device main body of the examination diagnosis device fitted to a support member.

FIG. 10 is an external perspective view showing the device main body 10a of the examination diagnosis device 10A fitted to the support member 50. As shown in FIG. 10, the grip 3 of the device main body 10a is fitted to the slider 51 of the support member 50. Thus, the outer peripheral surface of the grip 3 is in contact with the inner peripheral surface of the support member 50. In this state, the device main body 10a is movable in the Z direction with respect to the support member 50.

Figure 11:
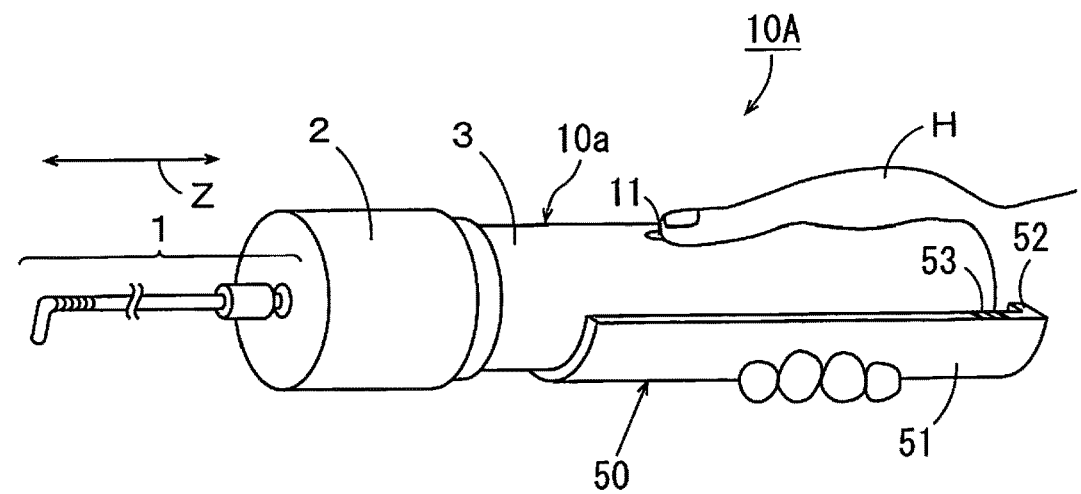
FIG. 11 is an external perspective view showing one example of the examination diagnosis device gripped by a user.

FIG. 11 is an external perspective view showing one example of the examination diagnosis device 10A gripped by the user. As shown in FIG. 11, the user holds the support member 50 with his or her first finger, second finger, third finger and fourth finger of his or her hand H and holds down the grip 3 of the device main body 10a with his or her thumb, thereby being able to grip the device main body 10a and the support member 50 together. In this case, it is possible to prevent the thumb from sliding with respect to the device main body 10a by placing the thumb at the recess 11. In this state, the user can move the device main body 10a forward and rearward in the Z direction with respect to the support member 50 by moving the thumb forward and rearward. The rearward movement of the device main body 10a is restricted by the stopper 52.

Figure 12:
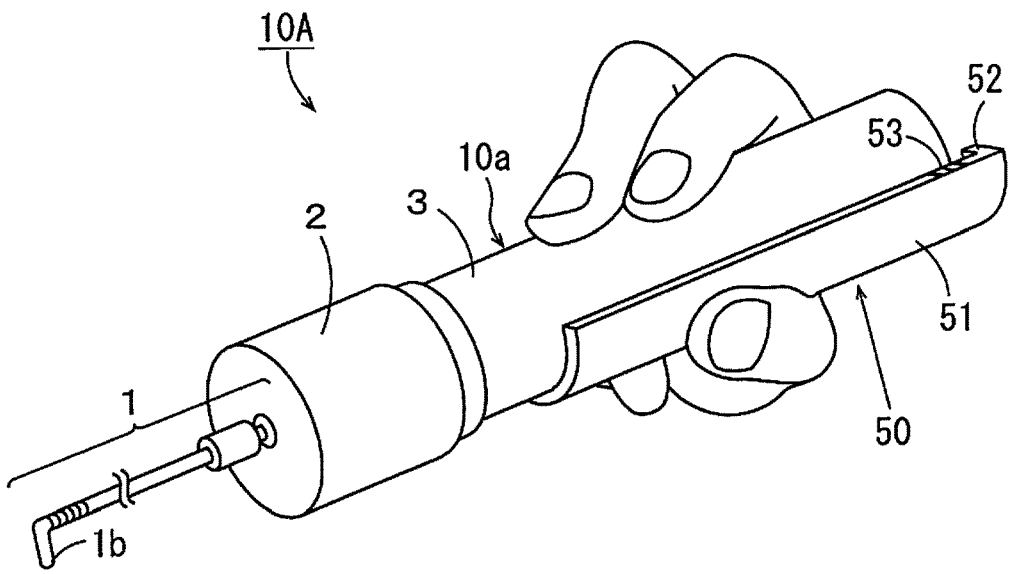
FIG. 12 is an external perspective view showing another example of the examination diagnosis device gripped by the user.

FIG. 12 is an external perspective view showing another example of the examination diagnosis device 10A gripped by the user. As shown in FIG. 12, the user holds the support member 50 using his or her thumb, third finger and fourth finger of his or her hand H, and holds down the grip 3 of the device main body 10*a* by the first finger and the second finger, thereby being able to grip the device main body 10*a* and the support member 50 together. In this case, it is possible to prevent the first finger and the second finger from sliding with respect to the device main body 10*a* by placing the first finger and the second finger at the recesses 11. In this state, the user can move the device main body 10*a* forward and rearward in the Z direction with respect to the support member 50 by moving the first finger and the second finger forward and rearward.

Figure 13:
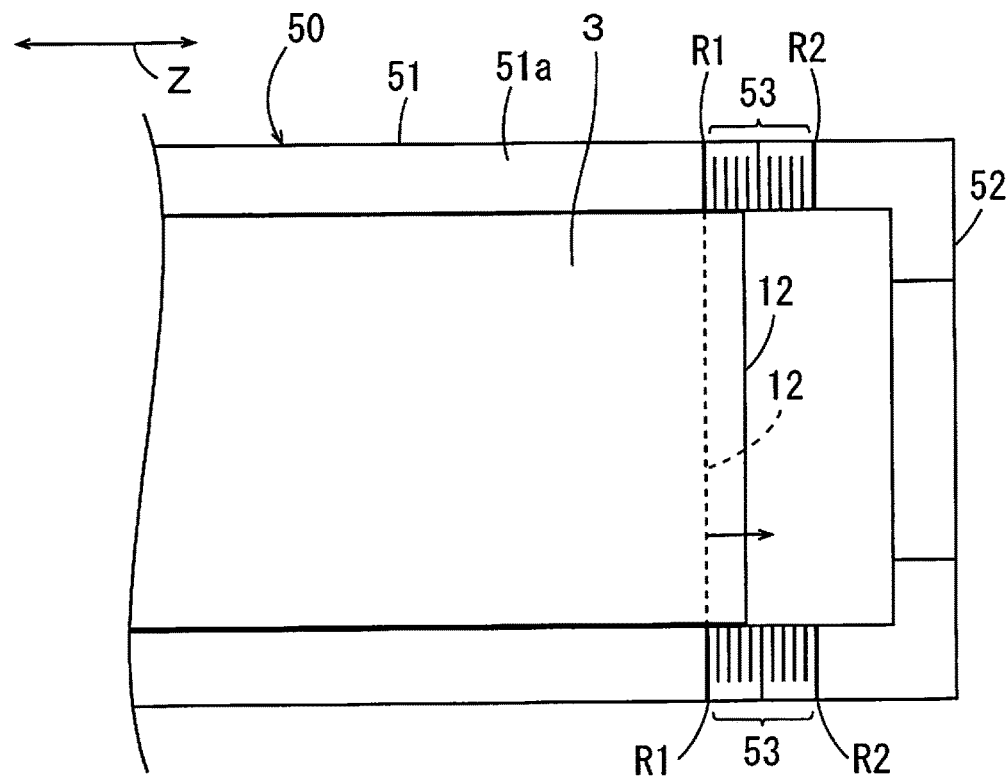
FIG. 13 is a partially enlarged plan view of a grip and the support member.

FIG. 13 is a partially enlarged plan view of the grip 3 and the support member 50. In FIG. 13, a scale mark at a front end of the movement amount measuring portion 53 is referred to as a first reference scale mark R1, and a scale mark at a rear end is referred to as a second reference scale mark R2.

Initially, the user allows a rear end surface 12 of the grip 3 to coincide with the first reference scale mark R1 of the movement amount measuring portion 53 as indicated by a dotted line. In this state, the user can pull the probe 1 rearward by moving the device main body 10*a* rearward with respect to the support member 50 as indicated by an arrow. Thus, the joint portion can be pulled by the probe 1. At this time, the user can identify a movement amount of the probe 1 by confirming which scale mark of the movement amount measuring portion 53 the rear end surface 12 of the device main body 10*a* is coinciding with. Further, the user allows the rear end surface 12 of the grip 3 to coincide with the second reference scale mark R2 of the movement amount measuring portion 53. In this state, the user can push the probe 1 forward by moving the device main body 10*a* forward with respect to the support member 50. Thus, the joint portion can be pressurized by the probe 1. At this time, the user can identify a movement amount of the probe 1 by confirming which scale mark of the movement amount measuring portion 53 the rear end surface 12 of the device main body 10*a* is coinciding with. Therefore, the user can easily adjust a length of pulling the probe 1 and a length of pushing the probe 1 to certain distances. Thus, it is possible to identify the force applied to the tip portion 1*b* of the probe 1 while ensuring reproducibility of the movement amount of the probe 1 during the examination and the diagnosis. As a result, the evaluation of the condition of the joint portion by pulling and pushing can be more accurately performed.

Further, when moving the device main body 10*a*, the user can identify the force applied to the tip portion 1*b* of the probe 1 and the movement amount of the probe 1 while feeling the force applied to the device main body 10*a* with his or her fingers. Thus, an appropriate movement amount of the probe 1 can be recognized for each patient.

Figure 14:
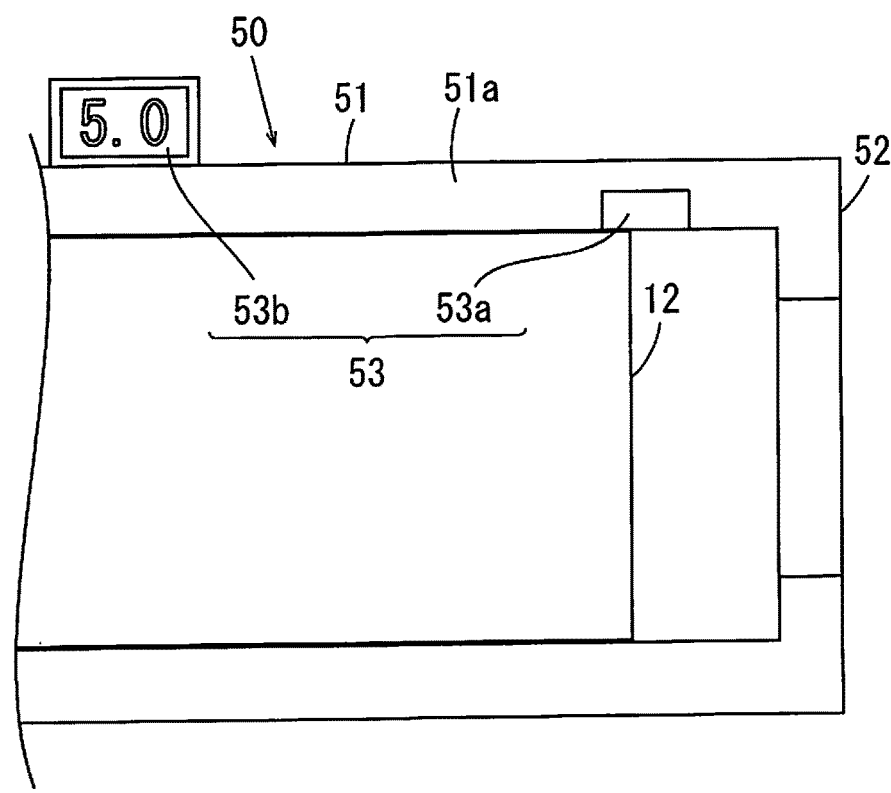
FIG. 14 is an enlarged plan view showing another example of a movement amount measuring portion.

FIG. 14 is an enlarged plan view showing another example of a movement amount measuring portion 53. The movement amount measuring portion 53 of FIG. 14 is constituted by a displacement sensor 53*a* and a display portion 53*b*. The displacement sensor 53*a* measures a movement amount (displacement) of the rear end surface 12 of the grip 3. As the display portion 53*b*, a liquid crystal display device is used, for example. The display portion 53*b* displays a movement amount measured by the displacement sensor 53*a* with a numeric value. Thus, the user can recognize the movement amount of the probe 1 by viewing the display portion 53*b*.

While the display portion 53*b* of the movement amount measuring portion 53 is attached to the support member 50 in the example of FIG. 14, the display portion 53*b* does not have to be attached to the support member 50. For example, the display 30 of FIG. 4 may display the movement amount measured by the displacement sensor 53*a*.

(7) Other Embodiments

While each of the A/D converter 20 and the display 30 is provided separately from the examination diagnosis device 10 in the above-mentioned first and second embodiments, the present invention is not limited to this. The A/D converter 20 may be provided in the examination diagnosis device 10, or both of the A/D converter 20 and the display 30 may be provided in the examination diagnosis device 10.

Further, in the above-mentioned first and second embodiments, the force Fz applied to the tip portion 1*b* of the probe 1 in the Z direction is detected, and the forces Fx, Fy applied to the tip portion 1*b* of the probe 1 in the X direction and the Y direction orthogonal to the Z direction are respectively detected. However, the present invention is not limited to this. The force applied to the tip portion 1*b* of the probe 1 in other directions intersecting with the Z direction may be detected instead of the forces Fx, Fy. For example, as shown in FIG. 8A, in the case where the tip portion 1*b* is bent in a direction that is not orthogonal to the elongated portion 1*a*, the force exerted in a direction parallel to the bending direction of the tip portion 1*b* may be detected.

In the above-mentioned first and second embodiments, the forces Fx, Fy in two directions, the X direction and the Y direction, are respectively detected in addition to the force Fz in the Z direction. However, the present invention is not limited to this. Only a force in one direction may be detected in addition to the force Fz in the Z direction, or forces in three or more directions may be detected in addition to the force Fz in the Z direction.

While the support member 50 and the device main body 10*a* can be separated from each other in the above-mentioned second embodiment, the device main body 10*a* may be attached to the support member 50 to be movable in the Z direction.

(8) Correspondences Between Constituent Elements in Claims and Parts in Preferred Embodiments In the following paragraphs, non-limiting examples of correspondences between various elements recited in the claims below and those described above with respect to various preferred embodiments of the present invention are explained.

In the above-mentioned embodiments, the examination diagnosis devices 10, 10A are examples of an examination diagnosis device, the grip 3 is an example of a grip, the stress detector 2 is an example of a detector, the probe 1 is an example of a probe, the tip portion 1*b* is an example of a tip portion, the Z direction is an example of a first direction, the X direction is an example of a second direction, and the Y direction is an example of a third direction.

As each of constituent elements recited in the claims, various other elements having configurations or functions described in the claims can be also used.

INDUSTRIAL APPLICABILITY

The present invention can be effectively utilized for examination and diagnosis of the condition of various joint portions.

The invention claimed is:

1. An examination diagnosis device for examining or diagnosing a condition of a joint portion, comprising:
   a probe that has a first end comprising a bent tip portion and an opposing second end;
   a grip to which the second end of the probe is connected such that the probe extends in a first direction;
   a detector that detects a force applied to the bent tip portion of the probe in the first direction, and detects a force applied to the bent tip portion of the probe in a second direction intersecting with the first direction;
   a support member that supports the grip, the grip being movable in the first direction with respect to the support member; and
   a scale for measuring a movement amount of the grip with respect to the support member, wherein
     the probe is formed such that a shape of the bent tip portion is retained when a force is applied to the bent tip portion,
     the grip has an outer peripheral surface extending in the first direction, and
     the scale is configured to move along the outer peripheral surface of the grip integrally with the support member when the grip moves with respect to the support member in the first direction.

2. The examination diagnosis device according to claim 1, wherein the tip portion of the probe is provided to be bent in a plane parallel to the first direction and the second direction.

3. The examination diagnosis device according to claim 1, wherein the detector detects a force applied to the tip portion of the probe in a third direction intersecting with the first direction and the second direction.

4. The examination diagnosis device according to claim 1, wherein the probe is formed of a rigid material.

5. The examination diagnosis device according to claim 1, wherein
   the support member includes a slider having an inner peripheral surface that is in contact with the outer peripheral surface of the grip,
   one end of the slider is open, and
   another end of the slider is provided with a stopper that is configured to stop movement of the slider.

6. An examination diagnosis device for examining or diagnosing a condition of a joint portion, comprising:
   a probe that has a first end comprising a bent tip portion and an opposing second end;
   a grip to which the second end of the probe is connected such that the probe extends in a first direction;
   a detector that detects a force applied to the bent tip portion of the probe in the first direction, and detects a force applied to the bent tip portion of the probe in a second direction intersecting with the first direction, wherein
   the grip has a pressure-receiving surface which extends in the second direction,
   the probe includes an elongated portion extending linearly, and the bent tip portion that is provided to be bent at one end of the elongated portion,
   another end of the elongated portion that is opposite to the bent tip is fixed to the pressure-receiving surface of the grip, and
   the detector includes a strain gauge type load cell that is provided in the grip and configured to detect the forces applied to the probe.

7. An examination diagnosis device for examining or diagnosing a condition of a joint portion, comprising:
   a probe that has a first end comprising a bent tip portion and an opposing second end;
   a grip to which the second end of the probe is connected such that the probe extends in a first direction;
   a detector that detects a force applied to the bent tip portion of the probe in the first direction, and detects a force applied to the bent tip portion of the probe in a second direction intersecting with the first direction;
   a support member configured to support the grip, the grip being movable in the first direction with respect to the support member; and
   a displacement sensor for measuring a movement amount of the grip with respect to the support member, wherein
   the probe is formed such that a shape of the bent tip portion is retained when a force is applied to the bent tip portion.

* * * * *